United States Patent
Gajewczyk et al.

(10) Patent No.: US 6,235,523 B1
(45) Date of Patent: May 22, 2001

(54) VECTORS FOR DNA IMMUNIZATION AGAINST CERVICAL CANCER

(75) Inventors: Diane M. Gajewczyk, Toronto; Roy Persson; Fei-Long Yao, both of North York; Shi-Xian Cao, Etobicoke; Michel H. Klein, Willowdale, all of (CA); James Tartaglia, Schenectady, NY (US); Phillipe Moingeon, F-Pommiers (FR); Benjamin Rovinski, Thornhill (CA)

(73) Assignee: Connaught Laboratories Limited, Toronto (CA)

( * ) Notice: Subject to any disclaimer, the term of this patent is extended or adjusted under 35 U.S.C. 154(b) by 0 days.

(21) Appl. No.: 09/390,027

(22) Filed: Sep. 3, 1999

Related U.S. Application Data

(60) Provisional application No. 60/099,291, filed on Sep. 4, 1998.

(51) Int. Cl.[7] .......................... A61K 39/12; A61K 48/00; C12N 15/09; C07H 21/04
(52) U.S. Cl. ..................................... 435/320.1; 424/204.1; 424/192.1; 424/186.1; 536/23.72; 514/44
(58) Field of Search ........................... 435/320.1; 514/44; 424/93.2, 192.1, 204.1, 186.1; 536/23.72, 24.3

(56) References Cited

U.S. PATENT DOCUMENTS 5,744,133 * 4/1998 Lathe et al. ........................... 424/93.2
6,004,557 * 12/1999 Edwards et al. .................... 424/192.1
6,013,258 * 1/2000 Urban et al. ....................... 424/186.1

OTHER PUBLICATIONS

Gariglio, P. et al. Therapeutic uterine–cervix cancer vaccines in humans. Arch. Med. Res. 29:279–184, 1998.*

Borysiewicz, L.K. et al. A recombinant vaccinia virus encoding human papillomavirus types 16 and 18, E6 and E7 proteins as immunotherapy for cervical cancer. The Lancet 347:1523–1527, 1996.*

McCluskie, M.J. et al. Route and method of delivery of DNA vaccine influence immune responses in mice and non–human primates. Mol. Med. 5:287–300, 1999.*

Kim, N. et al. Induction of cytotoxic T lymphocyte response against the E6 oncogene of human papillomavirus type 16 in C3H/HeJ mice. Mol. Cells 6:485–489, 1996.*

Boursnell, M.E.G. et al. Construction and characterisation of a recombinant vaccinia virus expressing human papillomavirus proteins for immunotherapy of cervical cancer. Vaccine 14:1485–1494, 1996.*

Crook, T. et al. Continued expression of HPV–16 E7 protein is required for maintenance of the transformed phenotype of cells co–transformed by HPV–16 plus EJ–ras. EMBO J. 8:513–519, 1996.*

Feltkamp, M.C.W. et al. Vaccination with cytotoxic T lymphocyte epitope–containing peptide protects against a tumor induced by human papillomavirus type 16–transformed cells. Eur. J. Immunol. 23:2242–2249, 1993.*

Ressing, M.E. et al. Human CTL epitopes encoded by human papillomavirus type 16 E6 and E7 identified through in vivo and in vitro immunogenicity studies of HLA–A*0201–binding peptides. J. Immunol. 154:5934–5943, 1995.*

* cited by examiner

Primary Examiner—Karen M. Hauda
Assistant Examiner—Quang Nguyen
(74) Attorney, Agent, or Firm—Sim & McBurney

(57) ABSTRACT

Vectors for DNA immunization against cervical cancer comprise a nucleic acid molecule encoding at least one non-toxic T-cell epitope of the E6 and/or E7 antigens of a strain of human papilloma virus (HPV) associated with cervical cancer, such as HPV-16, and a promoter operatively coupled to the nucleic acid molecule for expression of the nucleic acid molecule in a host to which the vector is administered.

7 Claims, 11 Drawing Sheets

FIG. 1B

Nucleotide Sequence of PCR Amplified dE7 from HPV-16

5' PCR Primer →

| | | | | |
|---|---|---|---|---|
| CTGCAGCAGG | CTAGCATGCA | TGGAGATACA | CCTACATTGC | ATGAATATAT |
| CAACCAGAGA | CAACTCAATT | GAATGACAGC | TCAGAGGAG | AGATGAAAT |
| GCTGGACAAG | CAGAACCGGA | CAGAGCCCAT | TACAATATTG | TAACCTTTTG |
| GACTCTCTAGC | TTCGGTTGTG | CGTACAAAGC | ACACACGTAG | ACATTGTAC |
| CTGTTAATGG | GCACACTAGG | AATTGTGTGC | CCCATCTGTT | CTCAGAAACC | ATAAGTTGAC |

← 3' PCR PRIMER pCMV-3 vector containing CMV promoter, Bovine Growth Hormone polyA and Kanamycin resistance

FIG. 5A pCMV3-HPVT#1

0.491 UG/UL, 50UL

Construction: A synthetic mini-gene with the following sequence was cloned into the polylinker between SalI and EcoRI of the CMV3 vector resulting in pCMV3-HPVT#1. The gene encodes a protein consisting of five HPV16 T-cell epitopes (From NH2-to COOH terminus), E7: 49-57, 11-20, 82-90, 86-93, and E6: 29-38. Three alanines were introduced between the epitopes. The start codon is in bold letters, the Kozak sequence underlined, and the stop codons in bolded italic letters.

SalI
<u>TCGACGCCGCCACCATGAGAGCCCATTACAATATTGTTACCTTTGCCGCCGCCTATATGTTA
GATTTGCAACCAGAGACAACTGAGCGCTCGTTAATGGCACACTAGGAATTGTGCCG
CGGGACACTAGGAATTGTGTGCCCATCGAGCGACCACTATACATGATAATATTAGA
ATGTGTGTAATAGTGAGAATTC</u>
        EcoRI

Translation of coding sequence:

```
         9          18          27          36          45          54
ATG AGA GCC CAT TAC AAT ATT GTT ACC TTT GCC GCC GCC TAT ATG TTA GAT TTG
 |   |   |   |   |   |   |   |   |   |   |   |   |   |   |   |   |   |
Met Arg Ala His Tyr Asn Ile Val Thr Phe Ala Ala Ala Tyr Met Leu Asp Leu
```

FIG.5A'

```
     63          72          81          90          99         100
CAA CCA GAG ACA ACT GCA GCC GCT CTG TTA ATG GGC ACA CTA GGA ATT GTG GCC ---
Gln Pro Glu Thr Thr Ala Ala Ala Leu Leu Met Gly Thr Leu Gly Ile Val Ala ---

117         126         135         144         153         162
GCG GCG ACA CTA GGA ATT GTG TGC CCC ATC GCA GCA GCC ACT ATA CAT GAT ATA ---
Ala Ala Thr Leu Gly Ile Val Cys Pro Ile Ala Ala Ala Thr Ile His Asp Ile ---

171         180
ATA TTA GAA TGT GTG TAA 3'
Ile Leu Glu Cys Val ***
```

FIG. 5B

A Synthetic HPV Epitopes Mini Gene

```
         49-57 E7
SalI    Kozak    Met (Arg Ala His Tyr Asn Ile Val Thr
TCGACGCGCCACCATGAGAGCCCATTACAATATGTTACC
          GCGGGGGGTGTACTCTCGGGTAATGTTATAACAATGG
                                III
         11-20 E7
Phe)Ala Ala Ala (Tyr Met Leu Asp Leu Gln Pro Glu Thr Thr)
TTTGCCGCCGCCTATATGTTAGATTTGCAACCAGAGACAACT
AAACGGCGGCGGATATACAATCTAAACGTTGGTCTCTGTTGA
     I
        82-90 E7
Ala Ala Ala (Leu Leu Met Gly Thr Leu Gly Ile Val) Ala Ala
GCAGCGCTCGTTAATGGGCACACTAGGAATTGTGGCCGCG
CGTCGCGAGCAATTACCCGTGTGATCCTTAACACCGGCGC
          VI
```

Ala(Thr Leu Gly Ile Val Cys Pro Ile)Ala Ala Ala(Thr Ile
GCGACACTAGGAATTGTGCCCATGCCAGCAGCCACTATA
CGGTGTGATCCTTAACACGGGTAGGTCGGTGATAT

V

29-38 E6
His Asp Ile Ile Leu Glu Cys Val) * * * *
CATGATATAATATTAGAATGTGTAATAGTGAG
GTACTATATTATAATCTTACACACATTATCACTCTTAA    RI

The mini-gene was assembled using five synthetic oligonucleotides (I-V, divided by arrows). The epitope sequences and the three alanine- spacers are indicated. The start codon ATG is in bold letters; the Kozak sequence, underlined: the stop codons, in stars.

SEQUENCE LISTING

<160> NUMBER OF SEQ ID NOS: 12

<210> SEQ ID NO 1
<211> LENGTH: 300
<212> TYPE: DNA
<213> ORGANISM: Artificial Sequence
<220> FEATURE:
<223> OTHER INFORMATION: Description of Artificial Sequence:Synthetic
      mini-gene

<400> SEQUENCE: 1
ctgcagcagg ctagcatgca tggagataca cctacattgc atgaatatat gttagatttg     60
caaccagaga caactcaatt gaatgacagc tcagaggagg aggatgaaat agatggtcca    120
gctggacaag cagaaccgga cagagcccat tacaatattg taaccttttg ttgcaagtgt    180
gactctacgc ttcggttgtg cgtacaaagc acacacgtag acattcgtac tttggaagac    240
ctgttaatgg gcacactagg aattgtgtgc cccatctgtt ctcagaaacc ataagtcgac    300

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence:Synthetic
      mini-gene

<400> SEQUENCE: 2
ctgcagcagg ctagcatgca tggagataca cct                                  33

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:Synthetic
      mini-gene

<400> SEQUENCE: 3
cagctgaata ccaaagactc ttgtctaccc cgtgt                                35

<210> SEQ ID NO 4
<211> LENGTH: 386
<212> TYPE: DNA
<213> ORGANISM: Artificial Sequence
<220> FEATURE:
<223> OTHER INFORMATION: Description of Artificial Sequence:Synthetic
      mini-gene

<400> SEQUENCE: 4
tcgacgccgc caccatgaga gcccattaca atattgttac ctttgccgcc gcctatatgt     60
tagatttgca accagagaca actgcagccg ctctgttaat gggcacacta ggaattgtgg    120
ccgcggcgac actaggaatt gtgtgcccca tcgcagcagc cactatacat gatataatat    180
tagaatgtgt gtaatagtga gaattcatga gagcccatta caatattgtt accttttgccg   240 ccgcctatat gttagatttg caaccagaga caactgcagc cgctctgtta atgggcacac    300
taggaattgt ggccgcggcg acactaggaa ttgtgtgccc catcgcagca gccactatac    360
atgatataat attagaatgt gtgtaa                                         386

<210> SEQ ID NO 5
<211> LENGTH: 180

```
<212> TYPE: DNA
<213> ORGANISM: Artificial Sequence
<220> FEATURE:
<223> OTHER INFORMATION: Description of Artificial Sequence:Synthetic

<400> SEQUENCE: 5
atgagagccc attacaatat tgttaccttt gccgccgcct atatgttaga tttgcaacca      60
gagacaactg cagccgctct gttaatgggc acactaggaa ttgtggccgc ggcgacacta    120
ggaattgtgt gccccatcgc agcagccact atacatgata taatattaga atgtgtgtaa    180

<210> SEQ ID NO 6
<211> LENGTH: 59
<212> TYPE: PRT
<213> ORGANISM: Artificial Sequence
<220> FEATURE:
<223> OTHER INFORMATION: Description of Artificial Sequence:Synthetic

<400> SEQUENCE: 6

Met Arg Ala His Tyr Asn Ile Val Thr Phe Ala Ala Ala Tyr Met Leu
  1               5                  10                  15

Asp Leu Gln Pro Glu Thr Thr Ala Ala Ala Leu Leu Met Gly Thr Leu
             20                  25                  30

Gly Ile Val Ala Ala Ala Thr Leu Gly Ile Val Cys Pro Ile Ala Ala
         35                  40                  45

Ala Thr Ile His Asp Ile Ile Leu Glu Cys Val
     50                  55

<210> SEQ ID NO 7
<211> LENGTH: 92
<212> TYPE: DNA
<213> ORGANISM: Artificial Sequence
<220> FEATURE:
<223> OTHER INFORMATION: Description of Artificial Sequence:Synthetic

<400> SEQUENCE: 7
tcgacgccgc caccatgaga gcccattaca atattgttac ctttgccgcc gcctatatgt     60
tagatttgca accagagaca actgcagccg ct                                   92

<210> SEQ ID NO 8
<211> LENGTH: 109
<212> TYPE: DNA
<213> ORGANISM: Artificial Sequence
<220> FEATURE:
<223> OTHER INFORMATION: Description of Artificial Sequence:Synthetic

<400> SEQUENCE: 8
ctgttaatgg gcacactagg aattgtggcc gcggcgacac taggaattgt gtgccccatc     60
gcagcagcca ctatacatga tataatatta gaatgtgtgt aatagtgag                109

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence:Synthetic

<400> SEQUENCE: 9
catataggcg gcggcaaagg taacaatatt gtaatgggct ctcatggtgg cggcg           55

<210> SEQ ID NO 10
<211> LENGTH: 46
<212> TYPE: DNA
```

-continued

```
<213> ORGANISM: Artificial Sequence
<220> FEATURE:
<223> OTHER INFORMATION: Description of Artificial Sequence:Synthetic

<400> SEQUENCE: 10
aatctaaacg ttggtctctg ttgacgtcgg cgagacaatt acccgt            46

<210> SEQ ID NO 11
<211> LENGTH: 100
<212> TYPE: DNA
<213> ORGANISM: Artificial Sequence
<220> FEATURE:
<223> OTHER INFORMATION: Description of Artificial Sequence:Synthetic

<400> SEQUENCE: 11
gtgatcctta acaccggcgc cggtgtgatc cttaacacac ggggtagcgt cgtcggtgat    60
atgtactata ttataatctt acacacatta tcactcttaa                        100

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:Synthetic

<400> SEQUENCE: 12
gtcgacttat ggtttctgag aacagatggg gcaca                        35
```

VECTORS FOR DNA IMMUNIZATION AGAINST CERVICAL CANCER

REFERENCE TO RELATED APPLICATIONS

This application claims priority pursuant to 35 USC 119(e) of U.S. Provisional Patent Application No. 60/099,291 filed Sept. 4, 1998.

FIELD OF THE INVENTION

The invention is concerned with immunotherapy of cancer, specifically cervical cancer.

BACKGROUND OF THE INVENTION

Cervical cancer is the second most common cause of cancer-related deaths in women worldwide. There is both epidemiological and experimental data which links the etiology of cervical cancer to infection with human papilloma virus (HPV) types 16 and 18. The HPV virus is prevalent in 35 to 40% of young women. Although treatment of early stage disease is relatively successful, recurrent disease is found in 15% of the patients. The outcomes of patients with recurrent disease are relatively poor. Hence, there is a need for a novel therapeutic approach (refs. 1, 2, 3—various references are referred to in parenthesis to more fully describe the state of the art to which this invention pertains. Full bibliographic information for each citation is found at the end of the specification, immediately preceding the claims. The disclosure of these references are hereby incorporated by reference into the present disclosure).

The strong association of HPV infection and cervical cancer suggests that a viral antigen-specific immunotherapeutic approach may be a feasible strategy in the treatment of cervical cancer. The goal of specific immunotherapy is to stimulate the immune response of a tumour-bearing patient to attack and eradicate tumour lesions. This strategy has been made feasible with the identification of tumour associated antigens (TAA). The strong association between HPV-16 infection and cervical cancer has made this disease a good candidate for immunotherapeutic intervention (ref. 4).

In HPV DNA-positive cervical cancers, the E6 and E7 oncogenic proteins are expressed. Experimental evidence suggests that these two proteins are responsible for the carcinogenic progression of cervical cancers as their expression leads to a transformed and immortalized state in human epithelial cell cultures (ref. 5). Therefore, these two proteins are potential candidates for antigen-specific immunotherapy in HPV-induced cervical cancers and are evaluated herein.

Although many questions remain regarding the nature of immunity to natural HPV infection, and, in turn, to cervical cancer, it is clear that there is an immune component as immunosuppressed individuals are at higher risk for developing a cervical malignancy (ref. 6). Furthermore, this immunity is most likely mediated by the cellular arm of the immune response. Extensive cellular infiltrates are observed upon examination of spontaneous regressions of cervical tumours (ref. 7). Thus, an antigen-specific cellular response appears to be required to treat cervical cancer patients.

Although the nature of the outcome of an immunotherapeutic strategy has been identified, the ability to induce this type of response using current vaccine technology is limited. Prophylactic vaccine development for HPV has focussed on recombinant subunit preparations consisting of L1 and L2 virion structural proteins. In eukaryotic cells, L1 (major capsid protein) organizes itself into papillomavirus-like particles (VLPS) (ref. 17). Although L1 alone is sufficient for assembly of VLPs, the coexpression of L2 (minor capsid protein) provides for greater capsid production (ref. 18). By contrast, therapeutic vaccine development has typically been directed to the expression of wild type E6 and/or E7 protein. Expression vectors employed include vaccinia virus (for example, as described in U.S. Pat. No. 5,744,133, (ref. 19, 20), alphavirus (for example U.S. Pat. No. 5,843,723), or other poxviruses (for example, U.S. Pat. No. 5,676,950). Therefore, a DNA vector encoding HPV antigens implicated in carcinogenic progression of disease was determined to be the optimal method by which a successful immunotherapeutic strategy could be achieved.

However, as previously noted the E6 and E7 HPV antigens are putatively oncogenic and thus immunization with a DNA construct encoding either or both of these proteins could result in the induction of further malignancy (refs. 5, 10, 11). Therefore, in order to minimize toxicity risks, a genetically detoxified E7 molecule was encoded herein in a DNA construct. This detoxified molecule is modified through the deletion of the retinoblastoma (Rb) binding region (refs. 8, 9). Another method of achieving antigen-specific immunity without the concomitant risks of oncogenic transformation is the use of an epitope strategy where only key parts of the molecule are administered to induce a specific immune response (refs. 12 to 16). This approach was used herein in the design of the DNA-polyepitope construct where a number of T-cell epitopes derived from both E6 and E7 are linked together. A comparison of these two approaches was made herein in a murine model of HPV-associated cervical cancer.

SUMMARY OF THE INVENTION

According to the invention, there are provided novel DNA constructs for the administration of HPV antigens to a host to provide an immune response in the host. The invention extends to methods of immunotherapy of HPV-caused tumor, particularly cervical cancer.

Antigens chosen for immunotherapy of HPV DNA-positive cervical cancers may be those expressed by such cancers. One such HPV antigen is the E7 antigen, which has previously been shown to have a protective ability in a vaccinia vector system.

Potential toxicity concerns exist with the use of a native form of E7 in a vaccine due to its ability to bind to the Rb protein and thus promote an oncogenic state. A novel detoxified version of E7 was constructed herein by deletion of the Rb binding site and incorporated into pCMV-3 (FIG. 2) to provide vector pCMV-dE7 (FIG. 1) for immunization.

The detoxified E7 coding sequence was prepared from the unmodified coding sequence by replacing approximately 210 bp with DNA formed from annealed oligos. The substitute sequence omitted a stretch of 18 nucleotides encoding the region of E7 involved in complex formation with cellular retinoglastoma (Rb) family proteins, namely amino acids 21 to 26 from the native E7 protein.

Immunization with the pCMV-dE7 construct resulted in significant protection from tumor outgrowth following engraftment of live C3 tumor cells expressing the wild-type E7 molecule, showing that the E7 DNA construct can be successfully used to stimulate protective immunity without any associated toxicity risks.

Another such HPV antigen is the E6 antigen. The antigens may be provided as full-length proteins or in the form of specific T-cell epitopes in the DNA constructs.

To evaluate the T-cell approach, a synthetic mini-gene was prepared containing nucleotide sequences encoding T-cell epitopes from both E6 and E7 proteins of HPV-16 (FIG. 5A). A DNA construct (pCMV3-HPVT#1) containing the mini-gene (FIG. 6) was used to immunize mice. Mice immunized with the DNA construct of FIG. 6 were 100% protected from tumor outgrowth.

The results from these studies indicate that DNA immunization can be used successfully to protect against live C3 tumor challenge and thus may be effective in the clinical treatment of cervical cancer.

Accordingly, in one aspect of the present invention, there is provided a vector comprising a nucleic acid molecule encoding at least one non-toxic T-cell epitope of the E6 and/or E7 antigen of a strain of human papilloma virus (HPV) associated with cervical cancer, such as HPV-16, and a promoter operatively coupled to the nucleic acid molecule for expression of the nucleic acid molecule in a host to which the vector is administered.

The promoter preferably is a cytomegalovirus promoter. The nucleic acid molecule may be contained within plasmid pCMV-3 which contains the immediate early cytomegalovirus promoter including enhancer and intron sequences, along with the bovine growth hormone polyA tail and a kanamycin resistance gene. The elements of pCMV-3 are shown in FIG. 2.

The nucleic acid molecule, in one embodiment, is an E7 antigen coding sequence detoxified to prevent oncogene replication in the host. The detoxification may be effected in any convenient manner, including removing from the native sequence, nucleic acid encoding the Rb binding site, including that encoding amino acids 21 to 26 of HPV-16. The vector containing such nucleic acid molecule may have the identifying characteristics of pCMV3-dE7, including the restriction map and construction elements as seen in FIG. 1.

The nucleic acid molecule, in another embodiment encodes E7 antigen epitopes comprising amino acids 11 to 20, 49 to 57, 82 to 90 and 86 to 93 and E6 antigen epitope comprising amino acids 29 to 38 of HPV-16. In particular, in this embodiment, the nucleic acid molecule may be that having SEQ ID No: 4 or 5 or may be that encoding an amino acid sequence having SEQ ID No: 6. The vector containing such nucleic acid molecule has the identifying characteristics of pCMV3-HPVT#1, including restriction map and construction elements as seen in FIG. 6.

The present invention, in another aspect, provides an immunogenic composition for in vivo administration to a host comprising a vector as provided herein, which may include a pharmaceutically-acceptable carrier therefor. The present invention, in a further aspect, provides a method of immunizing a host against cervical cancer caused by human papilloma virus (HPV), which comprises administering to the host an effective amount of the immunogenic composition of the invention. In an additional aspect, the present invention provides a method of treatment of a host having cervical cancer, which comprises administering to the host an effective amount of the immunogenic composition of the invention.

BRIEF DESCRIPTION OF THE DRAWINGS

FIG. 1B shows the nucleotide sequence (SEQ ID No: 1) of the PCR amplified dE7 from HPV-16 (pSE859.2). The 5' and 3' PCR primers (SEQ ID Nos: 2, 3) are indicated on this Figure by boxes;

FIG. 5A shows the nucleotide (SEQ ID No: 4, full length; SEQ ID No: 5, coding sequence) and derived amino sequence (SEQ ID No: 6) for a synthetic HPV mini-gene encoding a protein consisting of five HPV 16 T-cell epitopes (from NH$_2$— to —COOH terminus) E7: 49 to 57, 11 to 20, 82 to 90, 86 to 93, and E6: 29 to 38. Three alanines as spacers were introduced between each of the epitopes;

FIG. 5B shows the assembly of synthetic oligonucleotides containing HPV-16 epitopes from E6 and E7 to form the mini-gene of FIG. 5A. The five individual oligonucleotides are indicated as I to V (SEQ ID Nos: 7, 8, 9, 10, 11). The epitopes from E6 and E7 are indicated above the specific sequences and the numbers correspond to the amino acid sequence of the full length E6 and E7 proteins of HPV-16.

GENERAL DESCRIPTION OF INVENTION

Figure 1A:
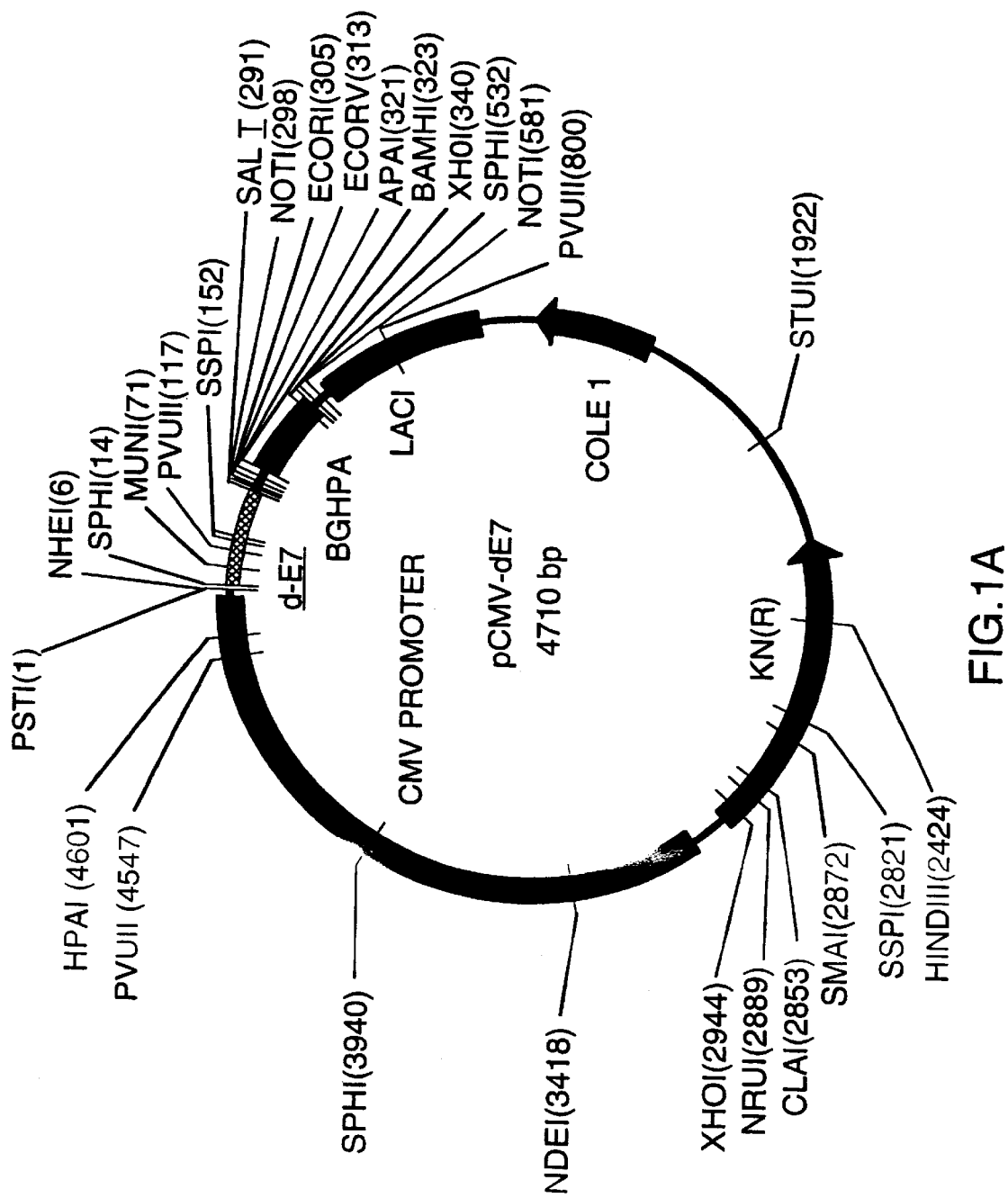
FIG. 1A is a map of a plasmid pCMV-dE7 comprising plasmid pCMV-3 with detoxified E7 from HPV-16 inserted therein.

The present invention provides an immunotherapy approach to cervical cancer caused by human papilloma virus (HPV) based on DNA immunization.

A series of experiments was conducted in the C3 cervical cancer model system. Using a DNA delivery platform, a number of E7 antigen based vaccines were evaluated for their ability to prevent tumour outgrowth following a live tumour cell challenge. Although the E7 antigen has been shown to have some protective ability in a vaccinia vector system, as noted above potential toxicity concerns exist with the use of a native form of E7 in a vaccine due to its ability to bind to the Rb protein and thus promote an oncogenic state. Therefore, a DNA construct encoding a "detoxified" version (dE7) of E7 of HPV-16 was constructed. Immunization with the dE7 DNA construct pCMV3-dE7, FIG. 1A) resulted in significant protection from tumour outgrowth following engraftment of live C3 tumour cells expressing the wild type E7 molecule. This finding indicates that a dE7 DNA construct could be used successfully to stimulate protective immunity without any associated toxicity risks.

An epitope-specific approach was also evaluated. A DNA construct composed of T-cell epitopes derived from both the E6 and E7 proteins of HPV-16 was used to immunize mice (pCMV3-HPVT#1, FIG. 6). Striking results were observed in the group of mice immunized with this polyepitope construct, in that 100% protection from tumour outgrowth was observed.

It is clearly apparent to one skilled in the art, that the various embodiments of the present invention have many applications in the fields of vaccination, diagnosis and treatment of HPV infections. A further non-limiting discussion of such uses is further presented below.

Vaccine Preparation and Use

Immunogenic compositions, suitable to be used as vaccines, may be prepared from the HPV genes, epitopes and vectors as disclosed herein. The vaccine elicits an immune response in a subject to induce a protective or therapeutic anti-tumor response. Immunogenic compositions, including vaccines, containing the nucleic acid may be prepared as injectables, in physiologically-acceptable liquid solutions or emulsions for polynucleotide administration. The nucleic acids in acceptable liquids may be utilized as direct immunizing agents (for example, as generally described in U.S. Pat. No. 5,589,466. Alternatively, the nucleic acid may be associated with liposomes, such as lecithin liposomes or other liposomes known in the art, as a nucleic acid liposome (for example, as described in WO 93/24640, ref. 21) or the nucleic acid may be associated with an adjuvant, as described in more detail below. Liposomes comprising cationic lipids interact spontaneously and rapidly with polyanions such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. Published PCT application WO 94/27435 describes compositions for genetic immunization comprising cationic lipids and polynucleotides. Agents which assist in the cellular uptake of nucleic acid, such as calcium ions, viral proteins and other transfection facilitating agents, may advantageously be used.

Polynucleotide immunogenic preparations may also be formulated as microcapsules, including biodegradable time-release particles. Thus, U.S. Pat. No. 5,151,264 describes a particulate carrier of a phospholipid/glycolipid/polysaccharide nature that has been termed Bio Vecteurs Supra Moleculaires (BVSM) . The particulate carriers are intended to transport a variety of molecules having biological activity in one of the layers thereof.

U.S. Pat. No. 5,075,109 describes encapsulation of the antigens trinitrophenylated keyhole limpet hemocyanin and staphylococcal enterotoxin B in 50:50 poly (DL-lactideco-glycolide). Other polymers for encapsulation are suggested, such as poly(glycolide), poly(DL-lactide-co-glycolide), copolyoxalates, polycaprolactone, poly(lactide-co-caprolactone), poly (esteramides), polyorthoesters and poly (8-hydroxybutyric acid), and polyanhydrides.

Published PCT application WO 91/06282 describes a delivery vehicle comprising a plurality of bioadhesive microspheres and antigens. The microspheres being of starch, gelatin, dextran, collagen or albumin. This delivery vehicle is particularly intended for the uptake of vaccine across the nasal mucosa. The delivery vehicle may additionally contain an absorption enhancer.

The vectors may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof.

Immunogenic compositions and vaccines provided herein may be administered parenterally, by injection subcutaneously, intravenously, intradermally or intramuscularly, possibly following pretreatment of the injection site with a local anesthetic. Alternatively, the immunogenic compositions, formulated according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as, for example, pharmaceutical grades of saccharine, cellulose and magnesium carbonate.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize the tumor associated antigens and antibodies thereto, and if needed, to produce a cell-mediated immune response. Precise amounts of active ingredient required to be administered depend on the judgement of the practitioner. However, suitable dosage ranges are readily determinable by one skilled in the art and may be of the order of about 1 $\mu$g to about 1 mg of the vectors. Suitable regimes for initial administration and booster doses are also variable, but may include an initial administration followed by subsequent administrations. The dosage may also depend on the route of administration and will vary according to the size of the host.

Immunogenicity can be significantly improved if the vectors are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Thus, adjuvants have been identified that enhance the immune response to antigens. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines.

A wide range of extrinsic adjuvants and other immuno-modulating material can provoke potent immune responses to antigens. These include saponins complexed to membrane protein antigens to produce immune stimulating complexes (ISCOMS), pluronic polymers with mineral oil, killed mycobacteria in mineral oil, Freund's complete adjuvant, bacterial products, such as muramyl dipeptide (MDP) and lipopolysaccharide (LPS), as well as monophoryl lipid A, QS 21 and polyphosphazene.

In particular embodiments of the present invention, the vector may be delivered in conjunction with a targeting molecule to target the vector to selected cells including cells of the immune system.

The polynucleotide may be delivered to the host by a variety of procedures, for example, Tang et al. (ref. 22) disclosed that introduction of gold microprojectiles coated with DNA encoding bovine growth hormone (BGH) into the skin of mice resulted in production of anti-BGH antibodies in the mice, while Furth et al. (ref. 23) showed that a jet injector could be used to transfect skin, muscle, fat and mammary tissues of living animals.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example describes the immunization protocol employed herein.

Female C57Bl/6 mice weighing 18 to 20 grams were obtained from Charles River (St. Constant, Quebec, Canada). The mice were housed in microisolators in accordance with guidelines as set out by the Canadian Council on Animal Care (CCAC). Ten animals were included in each treatment group. On Day 0, the mice were immunized with 100ug of each respective DNA construct, via either the intramuscular route (i.m.) in the anterior tibial muscle or the intradermal route (i.d.). The immunizations were repeated, with equivalent doses of each construct, on Days 21 and 42 of the study. Serum samples were obtained from mice on Days 20, 40 and 56.

Example 2

This Example describes the protocol for tumor cell challenge.

Two weeks following the last booster dose with the DNA construct following the procedure of Example 1, each mouse was injected subcutaneously (s.c.) in the nape of the neck with a dose of $5 \times 10^5$ live C3 tumour cells. The C3 tumour cell line was kindly provided by R. Offringa and C.Melief. The C3 cell line was created by transfecting B6 mouse embryo cells with the complete genome of HPV-16 was transformed with the ras oncogene. The expression of the HPV 16 oncogenic proteins E6 and E7 are required to maintain the transformed state.

After the injections were administered, the mice were examined three times per week for the duration of the study. Tumour measurements were taken using vernier calipers. The volume of the tumour mass was calculated using the following formula: volume=$ab^2/2$ where a=longer diameter and b=smaller measurement of the two. Mice that remained tumour free for a period of approximately three months following this initial live tumour cell challenge were then rechallenged on Day 141 of the study with the same dose and via the same route as the initial challenge on Day 57 described above. Following rechallenge, mice were monitored for the appearance of tumour outgrowth as described previously.

Example 3

This Example describes the E7 and dE7-specific IgG immunoassays (EIA).

Nunc Maxisorp immunoassay plates were coated overnight with either recombinant E7 or recombinant dE7 antigen at a concentration of 10 $\mu$g/mL diluted in 50 mM carbonate buffer pH 9.6. The next day the plates were washed in PBS containing 0.05% Tween 20 (PBS-T) and then blocked with 1% milk solution for one hour at room temperature. Following the blocking step, the plates were washed in PBS-T and the serum samples were added, at various dilutions, to the plates. The samples were incubated on the plates overnight at 4° C. The samples were washed off the plates the next day with PBS-T and a peroxidase-labelled sheep anti-mouse IgG conjugate was added at a dilution of 1/25,000 to each well. After a one hour incubation at room temperature, the plates were washed in PBS-T and the calorimetric reaction was developed using TMB substrate (ADI). The reactions were read at 450 nm in a Dynatech MR 5000 96-well plate reader.

Example 4

This Examples describes the construction of pCMV-dE7.

Figure 2:
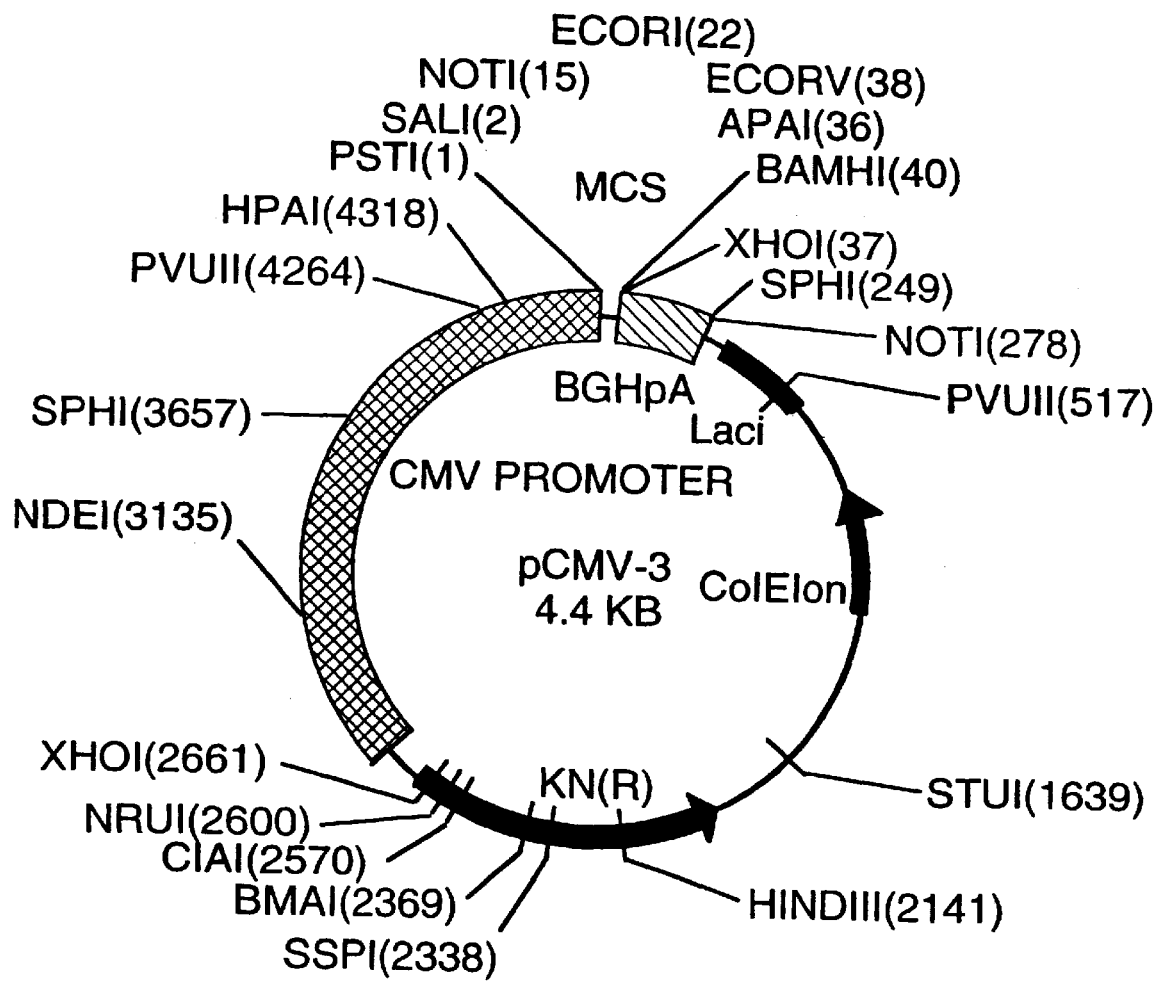
FIG. 2 is a map of plasmid vector pCMV3 containing the CMV immediate-early promoter including enhancer and intron sequences, bovine growth hormone polyA (BGH PA) and Kanamycin resistance (KN(R))
Figure 3A:
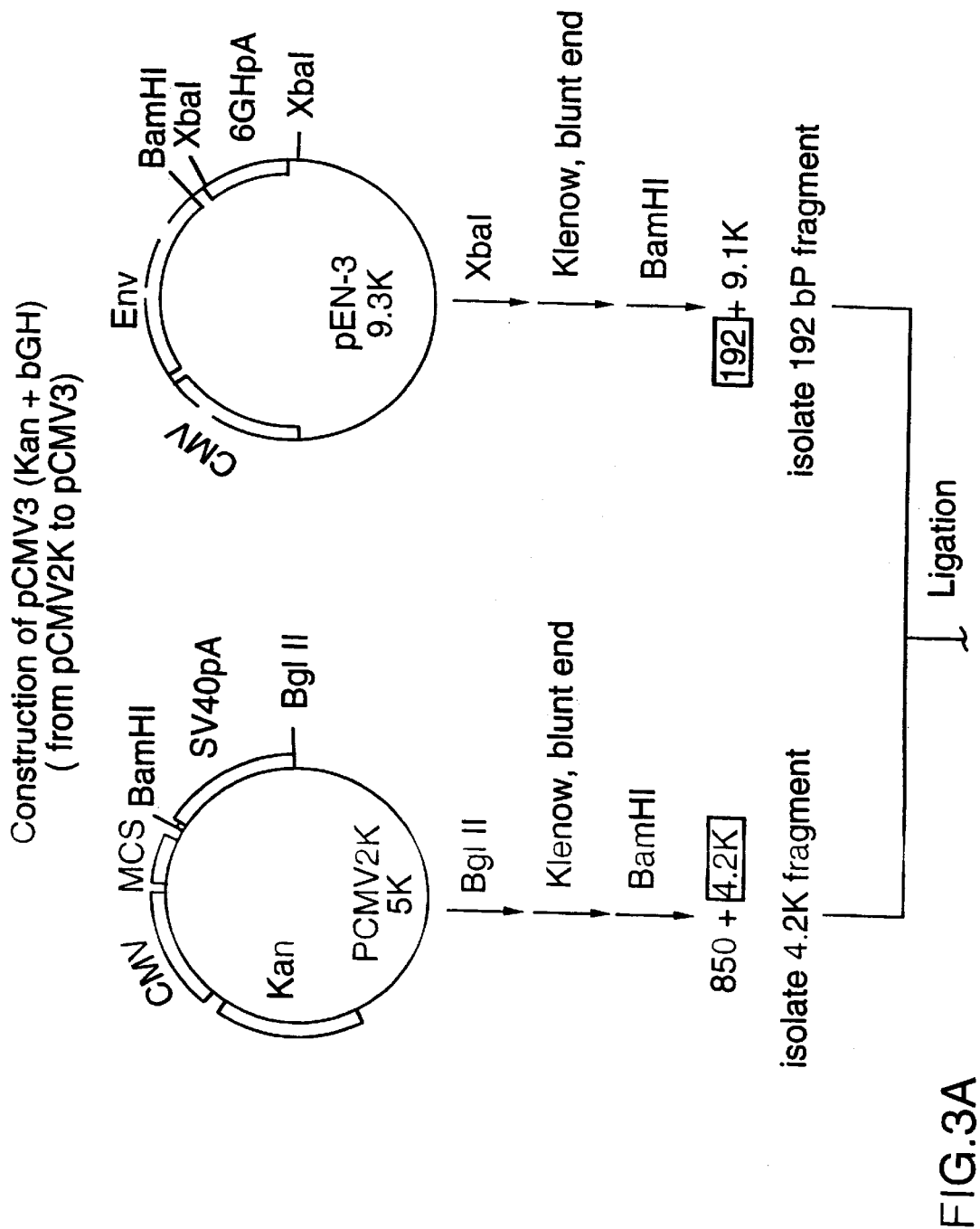
FIGS. 3A&B shows the assembly of plasmid vector pCMV3 from pCMV2K.
Figure 3B:
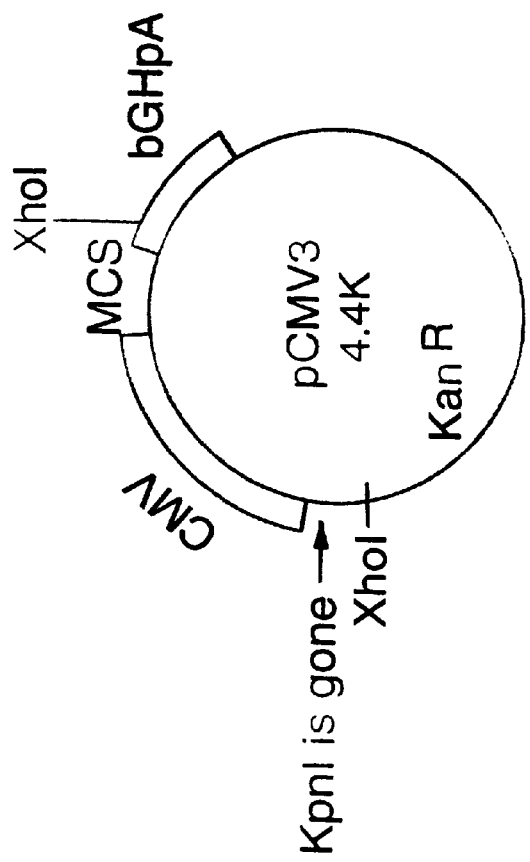

The plasmid pCMV3 contains segments from various sources and the elements of construction are depicted in FIG. 2. Briefly, the prokaryotic vector pBluescript SK (Stratagene) is the backbone of pCMV-3 and was modified by the replacement of AmPR gene with a $Kan^R$ gene and the deletion of the f1 and LacZ region. The modifications were achieved by deletion of the sequences between the restriction sites Ahd1 (nucleotide 2041) and Sac I (nucleotide 759) of pBluescript SK, which contains the $Amp^R$, f1 origin and the LacZ sequences. A 1.2 kb Pst I fragment from the plasmid pUC-4K (Pharmacia) containing the $Kan^R$ gene, was blunt end ligated to the Ahd I site of the modified pBluescript SK plasmid in a counter-clockwise orientation relative to its transcription. A 1.6 kb Ssp I/Pst I fragment containing the human cytomegalovirus immediate-early gene promoter, enhancer and intron A sequences (denoted CMV on FIG. 2) was ligated to the other end of the $Kan^R$ gene such that transcription from the CMV promoter proceeds in a clock-wise orientation. This procedure produced plasmid pCMV2K, as shown in FIG. 3.

Figure 4:
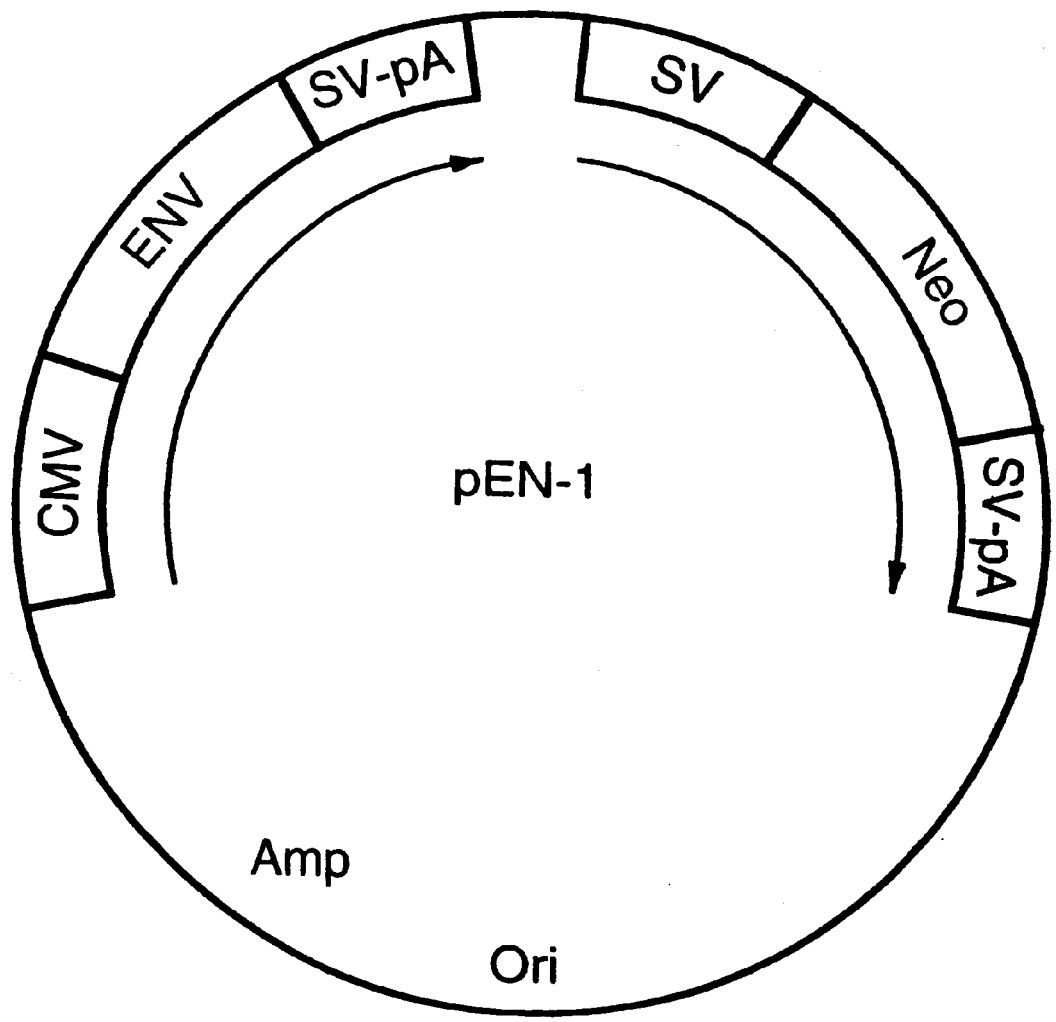
FIG. 4 is map of the plasmid vector pEN-1.

A 0.2 kb fragment containing the bovine growth hormone (BGH) polyadenylation signal sequence was removed from plasmid pEN-3 by Xba I restriction followed by klenow treatment to produce a blunt end and then Bam HI restriction. The 192 bp fragment containing the BGHpA fragment was isolated by agarose gel electrophoresis. Plasmid pEN-3 was prepared by cloning bGHpA into pEN-1 (FIG. 4).

Plasmid pCMV2K was then restricted with Bgl II, klenow treated and Bam HI restricted. The 4.2 kb fragment (see FIG. 3) was then isolated and ligated to the previously isolated 192 bp BGHPA fragment to produce plasmid pCMV3. The dE7 gene was then PCR amplified from plasmid pSE859.2 using primers that introduced a Pst I site at the 5' end (SEQ ID No: 2—CTGCAGCAGGCTAGCATGCATGGAGA TACACCT) and a Sal I site at the 3' end (SEQ ID No: 12—GTCGACTTATGGTTTCTGAGAACAGATGGGGCA CA). The amplified sequence is shown in FIG. 1B and contains detoxified E7 protein of HPV-16. The PCR fragment was inserted into pCR2.1 restricted with Pst I and Sal I (Invitrogen), and the insert sequenced (FIG. 1B). The Pst I to Sal I fragment was then subcloned into pCMV3 from Pst I to Sal I to produce plasmid pCMV-dE7 as shown in FIG. 1A.

Example 5

This Example illustrates the use of pCMV-dE7 to protect animals from tumour outgrowth following engraftment with a tumor cell line expressing wild type HPV-16 E7.

Mice were immunized with either a DNA construct encoding the detoxified E7 protein (pCMV-dE7, prepared as described in Example 4; FIG. 1), a DNA control (pCMV-3; FIG. 2) or PBS via the intramuscular route, following the protocol of Example 1. After three successive immunizations, live C3 tumour cells expressing the wild type E7 protein were engrafted at a dose of 5×10⁵ cells, following the protocol of Example 2. The number of mice tumour free following the challenge with live cells is shown in Table 1 below.

Approximately one month after challenge (Day 30), all the mice in the control groups (pCMV-3 control and PBS groups) had palpable tumours. In contrast, however, none of the mice in the pCMV-dE7 immunized group exhibited palpable tumours. By Day 60, one mouse of the pCMV-dE7 immunized group, who had previously been tumour negative, exhibited the initial indication of a palpable tumour. By Day 90, this mouse was euthanized due to the large tumour volume. The remaining mice of the pCMV-dE7 immunized group, however, remained tumour free. Thus, there was a significant difference observed in tumour free status between the mice in the dE7-immunized group and the control groups. The results thus indicate that immunization with a DNA construct encoding a genetically detoxified E7 molecule, (dE7) induced an immune response capable of protecting the animal against subsequent engraftment of live tumour cells.

TABLE 1

Percentage of Mice Tumour Free at Various Timepoints Following Live C3 Tumour Cell Engraftment

|  | Day 30 post challenge | Day 60 post challenge | Day 90 post challenge |
|---|---|---|---|
| CMV-dE7 | 100 | 90 | 90 |
| CMV-3 control | 0 | 0 | 0 |
| PBS | 0 | 0 | 0 |

Example 6

This Example illustrates that sera derived from mice immunized with the pCMV-dE7 construct are reactive with both the detoxified E7 and wild type E7 recombinant proteins.

In order to provide serological evidence that mice immunized with the genetically detoxified E7 protein according to Example 5 could generate immunity that was cross-reactive with the wild type E7 protein, sera from immunized mice was analyzed by EIA following the procedure of Example 3. The serum sample assayed was derived from a blood sample taken at Day 56, one day prior to live tumour cell challenge and two weeks following the last booster immunization.

The reactive antibody titre of the serum, as seen in Table 2 below, was equivalent whether it was assayed on a dE7-specific EIA or an E7-specific EIA. Thus, at the antibody level, the antibodies generated by immunization with dE7 were cross-reactive to the E7 protein.

TABLE 2

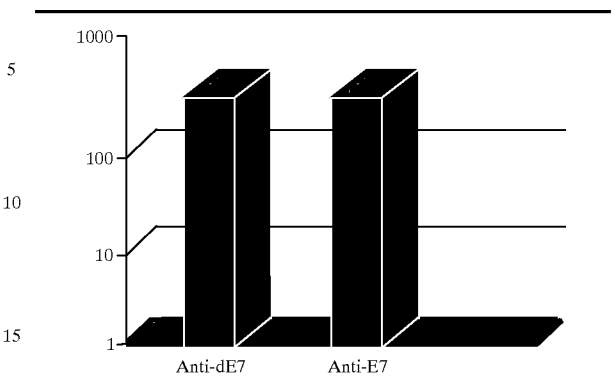

Example 7

This Example illustrates that the specific route of immunization has a significant effect on the induction of protective immunity.

The effect of the intramuscular (i.m.) route relative to the intradermal (i.d.) route of DNA immunization on the induction of antitumour immunity was investigated. Briefly, both groups of mice were immunized with the same construct (pCMV-dE7, prepared as described in Example 4; FIG. 1) at doses and frequency as described above in Example 1. However, one group was immunized via the i.m. route while the other group was immunized via the i.d. route. Following live C3 tumour cell challenge following the procedure of Example 2, the group immunized via the i.d. group exhibited tumour outgrowth, in direct contrast to the group immunized with via the i.m. route which remained tumour free. Thus, it was determined that DNA vaccination with the dE7 DNA construct elicited protective immunity against tumour cell challenge only when the immunization occurred via the i.m. route. The results are set forth in the following Table 3:

TABLE 3

Percentage of Mice Tumour Free following live C3 tumour cell engraftment

|  | Day 30 post challenge | Day 60 post challenge | Day 90 post challenge |
|---|---|---|---|
| CMV-dE7 i.m. | 100 | 90 | 90 |
| CMV-dE7 i.d. | 0 | 0 | 0 |

Example 8

This Example describes the preparation of plasmid pCMV3-HPVT#1.

Figure 6:
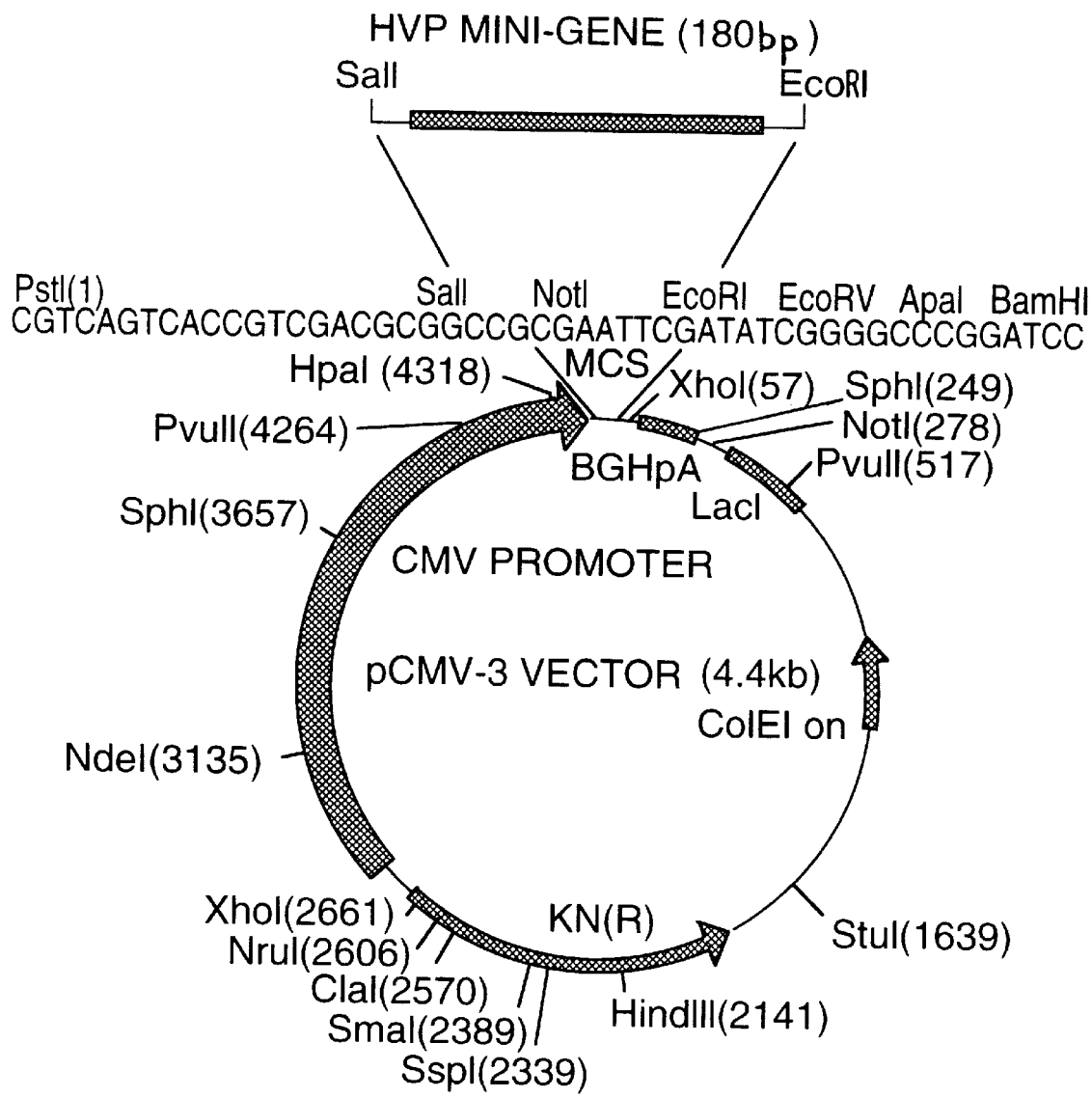
FIG. 6 shows the assembly of pCMV3-HPVT#1 by inserting the synthetic mini-gene shown in FIG. 5A into the polylinker between the SalI and EcoRI sites of the pCMV3 vector of FIG. 3.

The synthetic mini-gene encoding the five T-cell epitopes form HPV-16 E6 and E7 proteins (FIG. 5A) was constructed by oligonucleotide synthesis using an Applied Biosystems 3AB DNA synthesiser. The synthetic mini-gene assembled using five synthetic oligonucleotides (I to V, FIG. 5B) contained a Sal I restriction site at the 5' end and a Eco RI site at the 3' end. This assembled gene (FIG. 5) was cloned into the Sal I/Eco RI restricted plasmid pCMV3 to produce plasmid pCMV3-HPVT#1 as shown in FIG. 6. The construction of pCMV3 is described in Example 3 and the elements are shown in FIG. 2.

Example 9

This Example illustrates the use of pCMV3-HPVT#1 to induce protective antitumour immunity.

C57Bl/6 mice were immunized with either a DNA construct encoding multiple epitopes of the E6 and E7 proteins of HPV-16 (pCMV3-HPVT#1, prepared as described in Example 8; FIG. 6)or with controls (pCMV-3 vector alone, FIG. 2, or PBS), following the protocol of Example 1 Prophylactic immunization with the DNA polyepitope construct following the protocol of Example 2 induced protective antitumour immunity in 100% of the mice challenged. In contrast, there were no mice tumour free in the control groups. The results are set forth in the following Table 4.

TABLE 4

Percentage of Mice Tumour Free following live C3 tumour cell engraftment

|  | Day 30 post challenge | Day 60 post challenge | Day 90 post challenge |
| --- | --- | --- | --- |
| pCMV-polyepitope | 100 | 100 | 100 |
| PCMV-3 control | 0 | 0 | 0 |
| PBS | 0 | 0 | 0 |

Example 10

This Example illustrates the effect of a second rechallenge with live C3 tumour cells in mice tumour free three months following the initial live tumour cell challenge.

In order to determine if the protective antitumour immunity induced by either the pCMV-dE7 construct, prepared as described in Example 4 (FIG. 1), as seen n Example 7, or pCMV-polyepitope construct, prepared as described in Example 8 (FIG. 6), as seen in Example 9, was long-lived, mice that survived the initial tumour cell challenge and remained tumour free for period of three months were re-engrafted with live C3 tumour cells. The mice were then monitored for signs of tumour development.

As indicated in Table 5 below, one animal in the pCMV-dE7 group developed a tumour following this second challenge dose. However, all of the mice in the DNA-polyepitope immunized group remained tumour free. Thus, t he greatest level of protection from tumour cell challenge appeared to be in the polyepitope immunized group.

TABLE 5

Percentage of Mice Tumour Free following second live C3 tumour cell engraftment

|  | Day 30 post second tumour cell challenge | Day 60 post second tumour cell challenge |
| --- | --- | --- |
| PCMV-dE7 i.m. | 80 | 80 |
| PCMV-polyepitope i.m. | 100 | 100 |

SUMMARY OF DISCLOSURE

In summary of this disclosure, the present invention provides certain novel vectors containing nucleic acid encoding at least one T-cell epitope of E6 and/or E7 antigen of a strain of HPV associated with cervical cancer and method of immunization using such vectors. Modifications are possible within the scope of the invention.

REFERENCES

1. Pisani P. et al., Estimates of the worldwide mortality from eighteen major cancers in 1985. Implications for prevention and projections of future burden, Int. J. Cancer 1993:55:891–903.
2. Piver M. S., Handbook of gynecologic oncology. Boston: Little, Brown, 1996.
3. Kurman R. J. et al., Interim guidelines for management of abnormal cervical cytology. The 1992 National Cancer Institute Workshop, IAMA 1994-271:1866–9.
4. Bosch F X, et al., Prevalence of human papillomavirus in cervical cancer—a worldwide perspective. International biological study on cervical cancer (IBSCC) Study Group [see comments], J. Natl. Cancer Inst. 1995:87:796–802.
5. Pecoraso G. et al., Differential effects of human papillomavirus type 6, 16 and 18 DNAs on immortalization and transformation of human cervical epithelial cells. Proc. Natl. Acad Sci. USA, 1989:86:563–7.
6. Shamanin V., et al., Specific types of human papillomavirus found in benign preliferations and carcinomas of the skin in immunosuppressed patients, Cancer Res. 1994:54:4610–3.
7. Hilders C. G., et al., Association between HLA-expression and infiltration of immune cells in cervical carcinoma [see comments]. Lab. Invest. 1993:69:651–9.
8. Munger K., et al., Interactions of HPV E6 and E7 oncoproteins with tumour suppressor gene products. Cancer Surv. 1992:12:197–217.
9. Dyson N., et al. The human papilloma virus-16 E7 oncoprotein is able to bind to the retinoblastoma gene product. Science: 1989:243:934–7.
10. Munger K., et al. The E6 and E7 genes of the human papillomavirus type 16 together are necessary and sufficient for transformation of primary human keratinocytes. J. Virol 1989:63:4417–21.
11. Crook T., et al., Continued expression of HPV-16 E7 protein is required for maintenance of the transofmred phenotype of cells co-transformed by HPV-16 plus EJ-ras. EMBO. J. 1989:8:513–9.
12. Ressing M. E., et al., Human CTL epitopes encoded by human papillomavirus type 16 E6 and E7 identified through in vivo and in vitro immunogenicity studies of HLA-A*0201-binding peptides. J. Immunol. 1995:154:5934–5943.
13. Kast W. M., et al., Role of HLA-A motifs in identification of potential CTL epitopes in human papillomavirus type 16 E6 and E7 proteins. J. Immunol. 1994:152:3904–3912.
14. Feltkamp M. C., et al., Vaccination with cytotoxic T lymphocyta epitope-containing peptide protects against a tumor induced by human papillomavirus type 16-transformed cells. Eur. J. Immunol. 1993:23:2242–2249.
15. Alexander M., et al., Generation of tumor specific cytolytic T-lymphocytes from peripheral blood of cervical cancer patients by in vitro stimulation with a synthetic HPV-16 E7 epitope. Am. J. Obster. Gynecol 1996:175:1586–1593.
16. Steller M. A., et al., Human papillomavirus immunology and vaccine prospects. J. Natl. Cancer Inst. Monogr. 1996:21:145–148.
17. Schiller J. T., et al., Papillomavirus vaccines: current status and future prospects. Adv. Dermatol. 1996:11:355–80; discussion: 355–80; discusstion:381.
18. Kimbauer R., et al., Efficient self-assembly of human papillomavirus type 16 L1 and L1-L2 into virus-like particles, J. Virol. 1993:67:6929–6936.
19. Borysiewicz L. K., et al., A recombinant vaccinia virus encoding human papillomavirus type 16 and 18, E6 and E7 proteins as immunotherapy for cervical cancer [see comments]. Lancet 1996:347:1523–1527.
20. Irvine K. R., et al., Synthetic oligonucleotide expressed by a recombinant vaccinia virus elicits therapeutic CTL. J. Immunol. 1995:154:4651–7.
21. WO 93/24640
22. Tang et al., Nature 1992, 356:152–154.
23. Furth et al., Analytical Biochemistry, 1992, 205:365–368.

What we claim is:

1. A vector comprising a nucleic acid molecule encoding an HPV-16 E7 antigen lacking amino acids 21–26, wherein said nucleic acid molecule is operatively linked to a cytomegalovirus promoter.

2. The vector of claim 1 wherein said nucleic acid molecule is inserted into plasmid CMV-3.

3. The vector of claim 1 wherein said vector is pCMV-dE7.

4. A vector comprising a nucleic acid molecule encoding HPV-16 E7 antigen epitopes consisting of amino acids 11 to 20, 49 to 57, 82 to 90 and 86 to 93 and an HPV-16 E6 antigen epitope consisting of amino acids 29 to 38, wherein said nucleic acid molecule is operatively linked to a cytomegalovirus promoter.

5. The vector of claim 4 wherein said nucleic acid molecule consists of SEQ ID No: 4 or 5.

6. The vector of claim 4 wherein said nucleic acid molecule encodes an amino acid sequence consisting of SEQ ID No: 6.

7. The vector of claim 4 wherein said vector is pCMV3-HPVT#1.

* * * * *